United States Patent
Vurro et al.

(10) Patent No.: US 10,738,161 B2
(45) Date of Patent: Aug. 11, 2020

(54) POLYAMIDOAMINES WITH ANTIMICROBIAL ACTIVITY

(71) Applicant: ALFA-CM SRL, Milan (IT)

(72) Inventors: Sirio Vurro, Milan (IT); Paolo Ferruti, Milan (IT)

(73) Assignee: ALFA-CM SRL, Milan (IT)

( * ) Notice: Subject to any disclaimer, the term of this patent is extended or adjusted under 35 U.S.C. 154(b) by 0 days.

(21) Appl. No.: 16/321,839

(22) PCT Filed: Jul. 20, 2017

(86) PCT No.: PCT/EP2017/068343
§ 371 (c)(1),
(2) Date: Jan. 30, 2019

(87) PCT Pub. No.: WO2018/024494
PCT Pub. Date: Feb. 8, 2018

(65) Prior Publication Data
US 2019/0177480 A1    Jun. 13, 2019

(30) Foreign Application Priority Data

Aug. 2, 2016 (IT) ......................... 102016000081360

(51) Int. Cl.
C08G 73/02  (2006.01)
A61P 31/04  (2006.01)
A61P 31/10  (2006.01)

(52) U.S. Cl.
CPC ............ C08G 73/028 (2013.01); A61P 31/04 (2018.01); A61P 31/10 (2018.01)

(58) Field of Classification Search
CPC ......... C08G 73/028; A61P 31/10; A61P 31/04
See application file for complete search history.

(56) References Cited

U.S. PATENT DOCUMENTS 3,843,567 A * 10/1974 Matsunaga ............... C02F 1/26
521/28
2013/0243721 A1 * 9/2013 Ferruti .................. A61K 31/785
424/78.35

OTHER PUBLICATIONS

Barbucci, Polym. Amino Acid Residues, Macromolecules p. 37 (Year: 1986).*
Ferruti, Macromol. Rapid Commun. p. 332 23 No. 56 (Year: 2002).*
Ferruti P., "Poly(amidoamine)s: past, present and perspectives", Journal of Polymer Science, Part A: Polymer Chemistry, Mar. 1, 2013, pp. n/a-n/a.
Ferruti P., et al., "-Arginine polymers of poly(amidoamino acid) Structure: synthesis, acid/base properties and preliminary cytocompatibility and cell-permeating characterizations: -arginine polymers of poly(amidoamino acid)", Macromolecular Bioscience, vol. 14, No. 3, Nov. 8, 2013.
Search Report and Written Opinion of PCT/EP2017/068343 dated Oct. 23, 207.

* cited by examiner

*Primary Examiner* — Matthew P Coughlin
*Assistant Examiner* — Thurman Wheeler
(74) *Attorney, Agent, or Firm* — Silvia Salvadori, P.C.; Silvia Salvadori

(57) ABSTRACT

Disclosed are polyamidoamines having a number average molecular weight ranging between 1,000 Da and 200,000 Da, obtained by copolymerisation of N,N-methylenebisacrylamide, glycine and 4-aminobutylguanidine (agmatine), and having the following formula (I) wherein n and m are two numbers such that the value of (n+m) can range from 5 to 1,000, preferably from 20 to 200, and even more preferably from 45 to 55. The compounds according to the invention are useful as active ingredients of pharmaceutical compositions for the treatment and/or prevention of microbial infections, or as plant protection products to counteract bacterial and fungal pathogens in organic farming.

6 Claims, 10 Drawing Sheets

POLYAMIDOAMINES WITH ANTIMICROBIAL ACTIVITY

This application is a U.S. national stage of PCT/EP2017/068343 filed on 20 Jul. 2017, which claims priority to and the benefit of Italian Application No. 102016000081360 filed on 2 Aug. 2016, the contents of which are incorporated herein by reference in their entireties.

FIELD OF INVENTION

The present invention relates to novel polyamidoamines (PAAs) having antimicrobial activity which are obtained by copolyaddition of a mixture of glycine and 4-aminobutyl-guanidine (agmatine) with N,N-methylenebisacrylamide.

BACKGROUND TO THE INVENTION

Polyamidoamines (PAAs) are synthetic polymers obtained by Michael polyaddition, with a step mechanism, of primary or secondary amines and bisacrylamides, according to Scheme 1, which relates generically to the synthesis of PAAs from primary amines

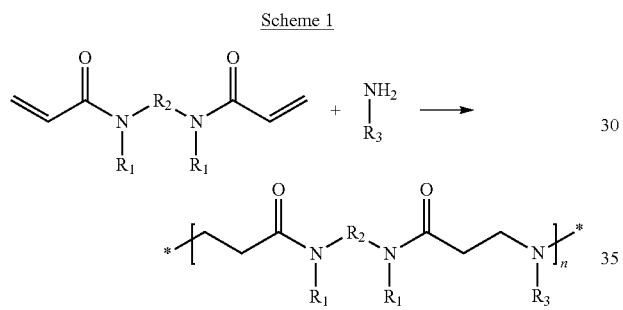

Scheme 1 wherein $R_1$ is hydrogen or an optionally substituted alkyl, $R_2$ is an alkylene, $R_3$ is an optionally substituted alkyl, and n is an integer that expresses the number of repetitive units required to give the polymer the desired molecular weight.

PAAs and methods for their preparation are described, for example, in WO2010/099962, WO2011/145056, P. Ferruti et al., *Biomacromolecules*, 2007, 8, 1498-1504, and P. Ferruti, *J. Polym. Sci. A*1 51, 2319-2353, (2013).

The polymerisation is usually conducted in water, in concentrated solution (≥25%), at room temperature, and in times ranging from 2 to 8 days. In special cases, other solvents such as alcohols, glycerin or mixtures of dimethylsulphoxide and water can be used. However, polar monomers such as amino acids, and the PAAs deriving from them, are generally poorly soluble in said solvents. Moreover, the polymerisation rates are often lower, and in most cases water is more convenient, if it can be used. In solvents without mobile hydrogen atoms, the polymerisation rate is modest, and the molecular weights of the products obtained are low.

Agmatine or 4-aminobutylguanidine (hereinafter called "G") is a compound deriving from decarboxylation of arginine, a natural amino acid containing a guanidine group, a very strong base, and a primary amino group of moderate basicity.

Agmatine reacts in aqueous solution with bisacrylamides, giving rise to a step polyaddition which, if the pH is maintained under 10, only involves the amino group, because under those conditions the guanidine group is protonated and does not react.

WO2011/145056 describes the copolymerisation of agmatine with 2,2-bis(acrylamido)acetic acid (Scheme 2). The resulting product, called AGMA-1, is a PAA whose side chains contain an amidino group, and which has antiviral activity.

Copolymerisation of agmatine with N,N-methylenebisacrylamide (hereinafter called "MBA") provides PAA containing guanidine groups called MBA-G) (Scheme 2):

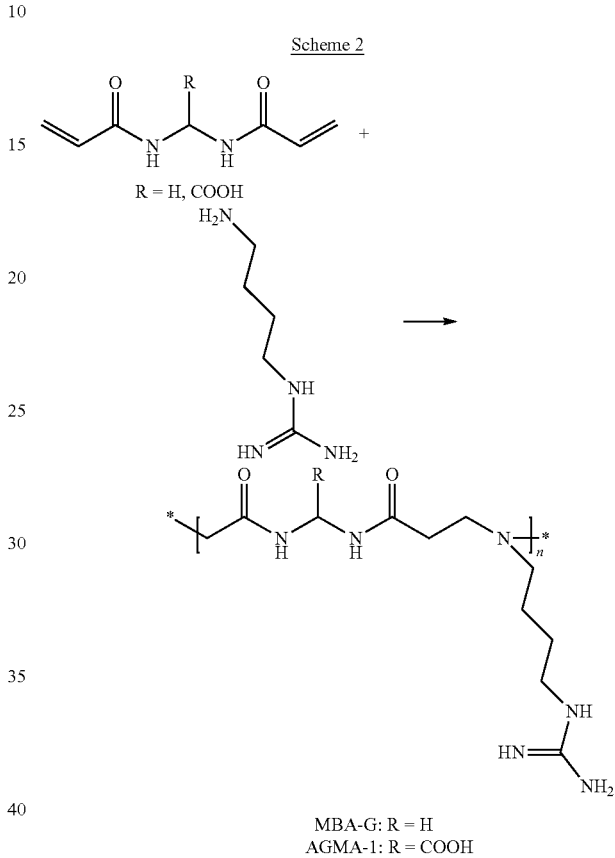

Scheme 2

MBA-G: R = H
AGMA-1: R = COOH

MBA-G is soluble in water and, like agmatine, is very basic. The inventors of the present invention have found that MBA-G possesses strong antimicrobial properties against many pathogenic micro-organisms.

A common characteristic of PAAs is that they form copolymers by copolyaddition of mixtures of different amines with the same bisacrylamide, or of the same amine with mixtures of different bisacrylamides. For example, the product obtained by copolymerising agmatine with mixtures of 2,2-bis(acrylamido)acetic acid and N,N-methylenebisacrylamide (MBA) contains both units in the same proportion as the two starting bisacrylamides, arranged randomly along the polymer chain, but both of them preceded and followed by a guanidine unit. All these copolymers are basic, but less than MBA-G, because they are internally buffered by the presence of carboxyl groups. The copolymers according to the invention (see below) constitute another example.

Among the amines usable as monomers in the synthesis of PAA, natural amino acids occupy a particular place. In their natural state they do not react with bisacrylamides, but if the pH of the mixture is increased to above 7.5-8, the reaction takes place. However, their reactivity is low, and PAAs with a fairly high molecular weight are only obtained if the reaction time is very long or the reaction conditions are forced by heating; however, in this case there is a risk of causing hydrolytic degradation reactions at the same time. Glycine is an exception, as it reacts at a rate comparable to that of the majority of amines.

DESCRIPTION OF THE INVENTION

Figure 1:
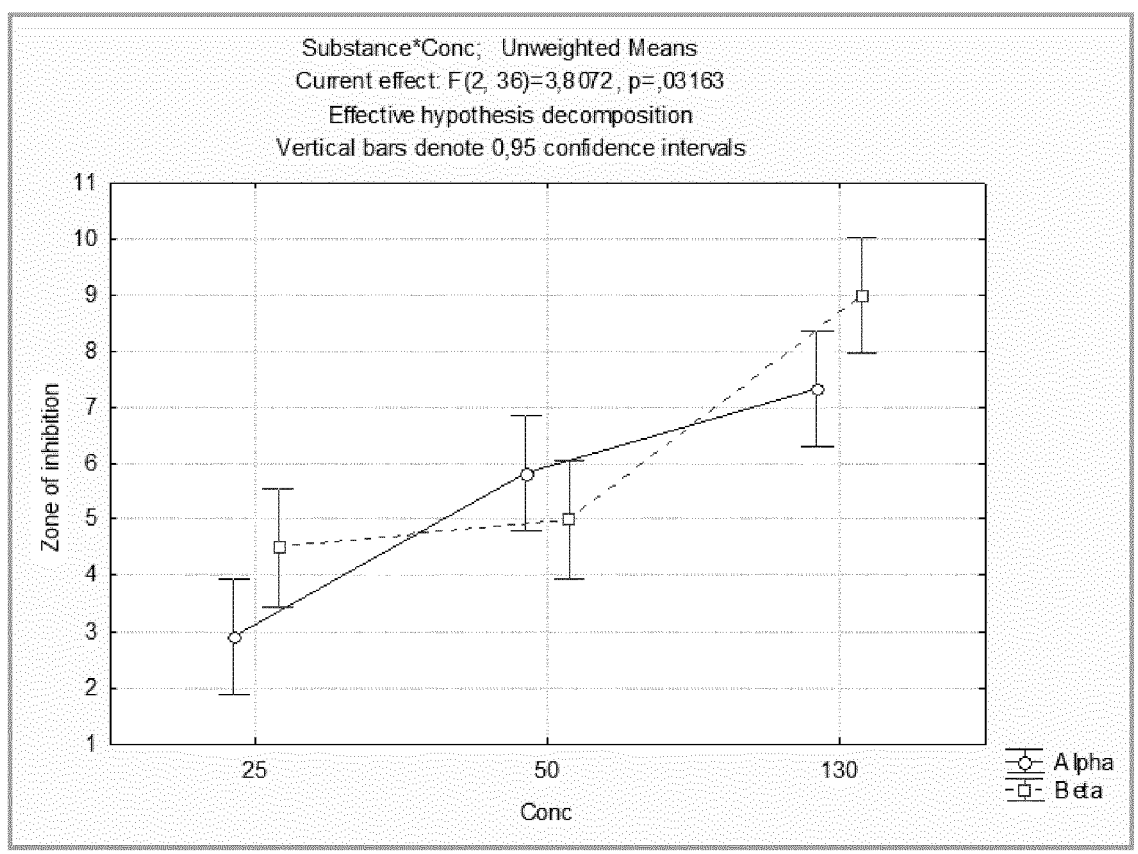
FIG. 1—Interaction of formulations α and β at different polyamidoamine concentrations (25, 50 and 130 μg/ml) to inhibit the growth (inhibition halo in mm) of various bacterial species (*B. licheniformis*; *P. syringae* pv *syringae*; *Xanthomonas* spp.). The data in the figure represent the mean of the data obtained with the various bacterial species.

It has now been discovered that PAAs obtained by copolyaddition of MBA with a mixture of glycine and agmatine maintain the antimicrobial activities of MBA-G, simultaneously reducing its toxicity to acceptable levels.

The PAAs according to the invention are copolymers having a number average molecular weight ranging between 1,000 Da and 200,000 Da, preferably between 5,000 Da and 30,000 Da, and even more preferably between 12,000 Da and 14,000 Da, obtained by copolymerisation of MBA, glycine and agmatine and having the following formula (I):

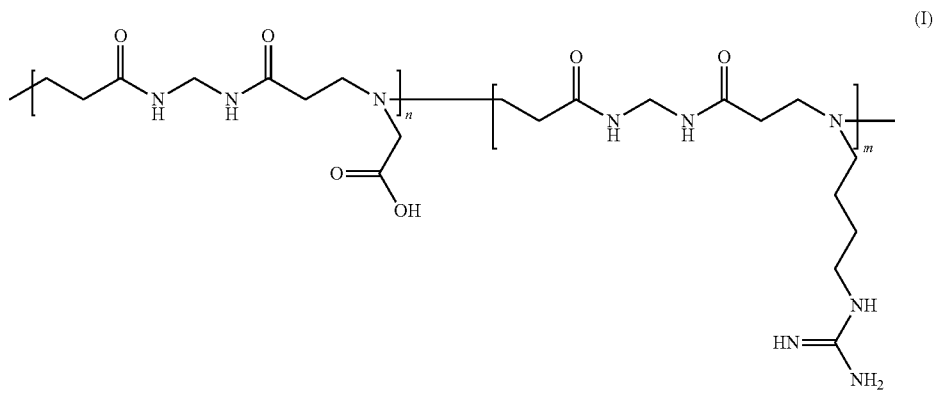

wherein n and m are two numbers such that the value of (n+m) ranges from 5 to 1,000.

The copolymers of formula (I) contain guanidine units and glycine units in the same proportions as the reaction mixture from which they derive, arranged randomly relative to one another along the polymer chain. According to the polymerisation mechanism (step polyaddition) in copolymers, the composition of the reaction product must exactly correspond to the starting mixture of monomers. The sum of (n+m) is an integer that expresses the average number of repetitive units required to give the polymer the desired molecular weight. For the copolymers of formula (I), (n+m) preferably ranges from 20 to 200 and even more preferably from 45 to 55, corresponding to number average molecular weights ranging, as stated, from 12,000 to 14,000 Da.

On average, the value of (n+m) in the copolymers examined is 50±5, which corresponds to number average molecular weights ranging from 12,000 to 13,500 Da. The precise value of the molecular weights is not critical for the purpose of the activity, whereas the ratio m/(n+m), namely the ratio between guanidine units and total units, is critical for that purpose. In the invention, the preferred ratio ranges from 0.25 to 0.7.

The ratio n/m can range from 0.05 to 99.5, preferably from 10 to 90, and even more preferably from 0.25 to 0.75.

In one embodiment of the invention, n/m is 0.75.
In another embodiment of the invention, n/m is 0.7.
In another embodiment of the invention, n/m is 0.6.
In another embodiment of the invention, n/m is 0.5.
In another embodiment of the invention, n/m is 0.4.
In another embodiment of the invention, n/m is 0.3.
In another embodiment of the invention, n/m is 0.25.

The PAAs according to the invention can be prepared by adding (n+m) molar equivalents of MBA to an aqueous solution containing n molar equivalents of glycine and m molar equivalents of an agmatine monoacid salt or diacid salt, wherein n and m are as defined above. The glycine and the agmatine diacid salt are neutralised by adding n and m molar equivalents respectively of a base inert to Michael addition such as an inorganic hydroxide or a tertiary amine.

The addition of the base to glycine in equimolecular quantities neutralises the carboxyl of the glycine, releasing the amino group, which can react as free base in the polyaddition reaction.

The addition of the base to the agmatine diacid salt in an equimolecular quantity moves a hydrogen atom of the acid used to salify the agmatine from the weaker base, the amino group, releasing it and enabling it to react, but leaves the much stronger guanidine group ionised, so that it does not interfere with the polyaddition reaction, which specifically involves the former. An agmatine monoacid salt, wherein the salification only involves the guanidine group, does not require neutralisation with the alkaline hydroxide.

Lithium monohydrate hydroxide is particularly convenient because it is easy to assay.

The agmatine diacid salt is preferably agmatine sulphate.

The polyaddition reaction is preferably conducted in water at a pH ranging between 8 and 10, reached if necessary with bases inert to Michael addition, such as inorganic hydroxides or tertiary amines, at a temperature ranging between 5° C. and 80° C., preferably between 10° C. and 30° C., for a time ranging between 3 and 300 hours, preferably between 24 and 192 hours.

The molecular weight of the resulting PAA is correlated with the stoichiometric ratio between the complementary polymerising functions (it is highest for equivalence ratios) and the reaction time.

The PAA is then isolated and purified by known procedures. Typically, the reaction mixture is diluted with water, acidified to a pH of 3-3.5, and finally ultrafiltered through a membrane with a suitable nominal cut-off at 1,000 Da, more typically at 5,000 Da. Finally, the retained fraction is freeze-dried and the fraction that passed through the membrane is eliminated.

The compounds according to the invention are effective against bacteria and fungi.

Examples of bacterial species sensitive to the effects of the compounds according to the invention are *E. coli, S. aureus, Xanthomonas* spp., *Pseudomonas syringae* pv. *Syringae, Bacillus licheniformis, B. subtilis* and *Pseudomonas* sp.

Examples of fungal species sensitive to the compounds according to the invention are *Monilia laxa, Monila fructigena, Botrytis cinerea* and *Monilinia fructicola*.

The compounds according to the invention are therefore useful as active ingredients of pharmaceutical compositions for the treatment and/or prevention of microbial infections.

The compounds according to the invention can be formulated with conventional carriers and excipients, which will be selected according to the usual practice.

The excipients can include surfactants, preservatives, antioxidants, chelating agents, carbohydrates, hydroxyalkylcellulose, hydroxyalkylmethylcellulose, poloxamer, polymeric stabilisers and the like.

The pharmaceutical compositions according to the invention comprise at least one compound of formula (I) together with one or more carriers and/or excipients. The pharmaceutical compositions include those suitable for various administration routes, such as the oral, topical, intravenous and parenteral routes. The pharmaceutical compositions can conveniently be in dose unit form, and can be prepared by well-known methods.

When employed for oral uses, tablets, pastilles, aqueous or oily suspensions, granules or dispersible powders, hard or soft capsules, syrups or elixirs can be prepared. The compositions designed for oral use can be prepared by any known method for the preparation of pharmaceutical compositions, and said compositions can contain one or more sweeteners, flavouring agents, colorants and preservatives, to provide a preparation with a pleasant flavour.

For topical administration, for example through the mucosa and skin, the pharmaceutical compositions are preferably applied as ointments, gels, creams or pastes containing the compounds according to the invention. The topical formulations can include a compound that facilitates the absorption or penetration of the compounds according to the invention through the skin or other affected areas, or other antimicrobial agents.

The compositions suitable for parenteral administration include sterile aqueous and non-aqueous injectable solutions, or suspensions containing the compounds according to the invention.

The daily dose of the PAAs according to the invention can range from 10 to 10,000 mg, preferably from 100 to 1,000 mg. The dose can be corrected on the basis of efficacy, pharmacokinetic and toxicological studies.

The compounds according to the invention can also be used as plant protection products to counteract bacterial and fungal pathogens in organic farming.

For use as plant protection products, the compounds according to the invention can be formulated in solid or liquid form.

Examples of solid formulations for agricultural use are:
water-dispersible granules and soluble granules, wherein the compounds according to the invention, suitably selected dispersing agents and inert agents, are ground together to obtain a homogeneous pre-mixture which can then be granulated by different technologies, such as extrusion and agglomeration;
wettable powders and soluble powders, obtained by mixing the compounds according to the invention with the most suitable dispersing agents, wetting agents and inert substances, and grinding the ingredients together.

Examples of liquid formulations for agricultural use are:
concentrated aqueous suspensions or dispersions in oil, wherein the compounds according to the invention are finely ground and homogeneously dispersed in water or oil with the aid of dispersing agents and wetting agents; the formulation is completed by thickeners and antifoaming agents;
emulsifiable liquids, wherein the compounds according to the invention are dissolved in the most suitable solvent together with emulsifiers;
oil/water emulsions, wherein the compounds according to the invention and a suitable solvent are emulsified in water by stirring at high shear rates in the presence of a small quantity of surfactant; the formulation is completed by thickeners and antifoaming agents;

microemulsions, wherein the compounds according to the invention and a suitable solvent are spontaneously emulsified in water by means of a large quantity of surfactants;

suspensions of microcapsules, wherein the compounds according to the invention, and optionally a small portion of a suitable solvent, are suspended in water in the form of small drops surrounded by a semipermeable plastic film which allows their controlled release.

The invention will now be illustrated in more detail by the following examples.

EXAMPLES

Example 1: Synthesis of the Polyamidoamine GUAGLY 5:5

Glycine (7.51 g, one-tenth of a mole) is dissolved in 50 mL of distilled water to which lithium hydroxide monohydrate is added (4.2 g, one-tenth of a mole).

A mixture of agmatine sulphate (22.83 g, one-tenth of a mole) and 75 mL of water is prepared separately, and lithium hydroxide monohydrate (4.2 g, one-tenth of a mole) is added under stirring. The mixture gradually becomes a homogeneous solution.

The two solutions are combined, solid N,N-methylenebisacrylamide (30.82 g, two-tenths of a mole) is added, and the mixture is stirred at room temperature (about 20° C.) until a homogeneous solution is obtained. Stirring is stopped at this point and the mixture is left to stand for seven days, stirring it from time to time to prevent uneven concentrations in the solution which, when reacting, becomes increasingly viscous.

At the end of the reaction the mixture is diluted to 600 mL with distilled water, acidified with hydrochloric acid to pH 3-3.5 and ultrafiltered through a membrane with a nominal cut-off of 5,000 Da (process also feasible at 1,000 Da). The retained fraction is freeze-dried, and the fraction that passed through the membrane is eliminated.

35 g of product with a number average molecular weight of 12,800 Da and a polydispersity of 1.26 is obtained. Said values were obtained by size exclusion chromatography (SEC) using a Knauer Pump 1000 equipped with a Knauer Autosampler 3800, TKSgel G4000 PW, and G3000 PW TosoHaas columns connected in series, a Viscotek 270 Dual Detector (light scattering/viscometer) and a Waters model 2410 refractive index detector. The mobile phase was an 0.1 M pH 8.1±0.05 Tris buffer containing 0.2 M sodium chloride. The concentration of the sample was 20 mg/mL, and the flow rate was 1 mL/min.

By using the procedure described above and suitably varying the molar ratios between MBA, agmatine (GUA) and glycine (GLY), but maintaining the stoichiometric equivalence between their sum and the MBA, the products shown in the Table are obtained.

TABLE

| Code | Moles of MBA | Moles of GUA | Moles of GLY | Number average molecular weight and polydispersity (PD) |
|---|---|---|---|---|
| GUAGLY-7:3 | 1 | 0.7 | 0.3 | 13,300 (PD = 1.32) |
| GUAGLY-6:4 | 1 | 0.6 | 0.4 | 13,500 (PD = 1.28) |
| GUAGLY-5:5 | 1 | 0.5 | 0.5 | 12,800 (PD = 1.26) |
| GUAGLY-4:6 | 1 | 0.4 | 0.6 | 14,100 (PD = 1.32) |
| GUAGLY-3:7 | 1 | 0.3 | 0.7 | 13,800 (PD = 1.35) |
| GUAGLY-2.5:7.5 | 1 | 0.25 | 0.75 | 12,700 (PD = 1.30) |

Example 2—Evaluation of Antibacterial Activity

Tests were conducted by the agar diffusion method according to standard SNV-195920—1992 on the *E. coli* and *S. aureus* bacterial strains.

The compounds used for the tests were:
A) GUAGLY-5:5
B) MBA-Agmatine (comparator compound)

The zones of inhibition of bacterial growth obtained on cotton gauze 100% impregnated with the test compound solution are well defined, and indicate good efficacy of both compounds against the *E. coli* and *S. aureus* bacterial strains.

Example 3—Evaluation of Antibacterial Activity Against *S. aureus*

Using the same agar diffusion method, tests were conducted on *S. aureus*, modifying the concentrations of the following compounds α, β:

α (MBA 1.0 AGMATINE 0.5 GLYCINE 0.5) (GUAGLY-5:5)
β (MBA 1.0 AGMATINE 0.6 GLYCINE 0.4) (GUAGLY-6:4)

The concentrations tested were 12.5 and 3.125 μg/ml.

PAAs α and β exhibit a well-defined inhibition halo of bacterial growth at both concentrations, with fairly good antibacterial activity at the lower concentration and good activity at the higher concentration.

Example 4—Antimicrobial Activity of GUAGLY-5:5 (α) and GUAGLY-6:4 (β) Against Pathogenic Plant and Animal Strains As regards plant pathogens, the antimicrobial activity of the compounds according to the invention was measured against various bacteria, such as *Xanthomonas* spp. (XJ), *Pseudomonas syringae* pv. *Syringae* (PSS1), *Bacillus licheniformis* (Blich), *B. subtilis* (Bsub) and *Pseudomonas* sp. (C99), and the fungal species *Botrytis cinerea* (Bc) and *Monilinia fructicola* (Mfruct). The disc diffusion test of Example 2 was used. In particular, 100 μl of cell suspension containing $10^4$ bacterial cells or conidial cells was diffused on discs of nutrient agar or potato dextrose agar. Sterile filter paper discs with a diameter of 25 mm were then deposited in the centre of each plate and impregnated with 150 μl of polymer at different concentrations (25, 50, 100, 130 and 150 μg/ml). In the control plates, the paper was impregnated with sterile distilled water. The experiments were conducted in triplicate for each antimicrobial agent and each concentration. The plates were incubated at room temperature for 24 and 48 h for the bacteria and fungi respectively. The activity was determined by measuring the inhibition halo round the paper disc in mm.

The experiments were organised according to a wholly random plan, and the data subjected to factorial analysis of variance taking account of the type of substance, the concentration and the microbial species as main factors. The value P≤0.05 was used to discriminate the statistical significance and the means of treatment compared to use the confidence interval.

To evaluate the activity of the substances in limiting the development of grey mould and root rot, twenty apples were sterilised on the surface with a 2% sodium hypochlorite solution for 2 min., rinsed with tap water and left to dry, then damaged by making one lesion 2 mm wide and 2 mm deep on each fruit, along the equator. *B. cinerea* and *M. fructicola*, cultured on potato dextrose agar (PDA) for 7-10 days at 22° C., were used to prepare a spore suspension (5×10$^4$ spores/ml) in sterile distilled water containing 0.05% Tween 80. The lesions were inoculated with 20 µl of the pathogen spore suspension, and the apples were left under a laminar-flow hood. Two hours later, 100 µl of α-polyamidoamine solution at different concentrations (100 and 150 µg/mL) was inoculated into each lesion. Lesions treated with sterile distilled water were used as control. The fruit was stored at 20° C. and high RH (90%) for seven days, after which the number of infected apples were recorded.

Results

The PAA concentration clearly influences the inhibition halo of the bacterial strains examined: inhibition increased with concentration and was dependent on the type of PAA (α or β) used in the experiment (FIG. 1).

Figure 2:
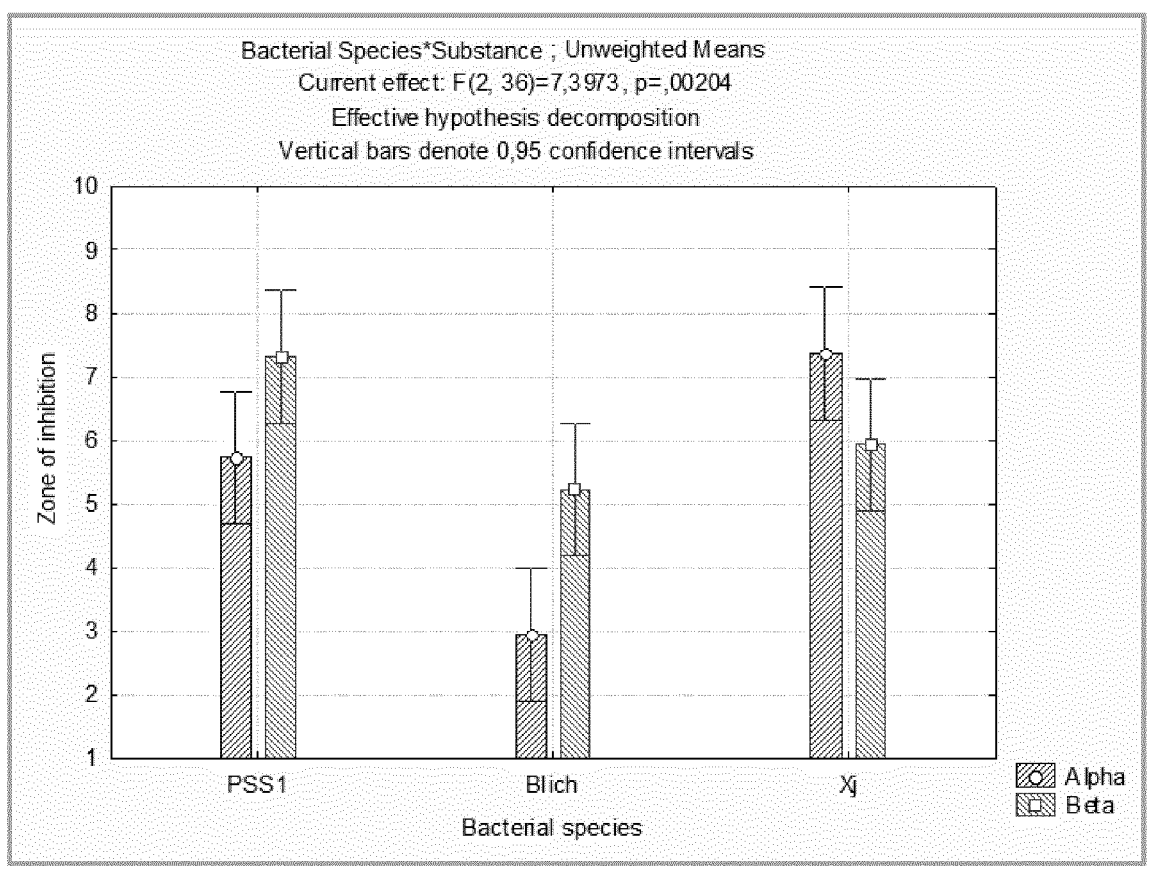
FIG. 2—Effect of two different polyamidoamine formulations (α and β) on the inhibition halo (in mm) of different bacterial species (Blich=*B. licheniformis*; PSS1=*P. syringae* pv *syringae*; XJ=*Xanthomonas* spp.). For each bacterial species and polyamidoamine formulation, the means of the results obtained at different concentrations (25, 50, and 130 μg/ml) are reported.

PAAs α and β proved very effective as inhibitors of the bacterial species *P. syringae* pv *syringae* and *Xanthomonas* spp., but somewhat less effective towards the species *B. licheniformis* (FIG. 2). The figure shows the sensitivity of the bacterial strains exposed to the PAAs, and the graphs represent an interpolation obtained with concentrations of 25, 50 and 130 µg/ml.

Subsequent tests conducted with higher concentrations of PAA (100 and 150 µg/ml) clearly indicate that when the concentration is increased, the inhibitory power against pathogenic bacteria also increases.

Figure 3:
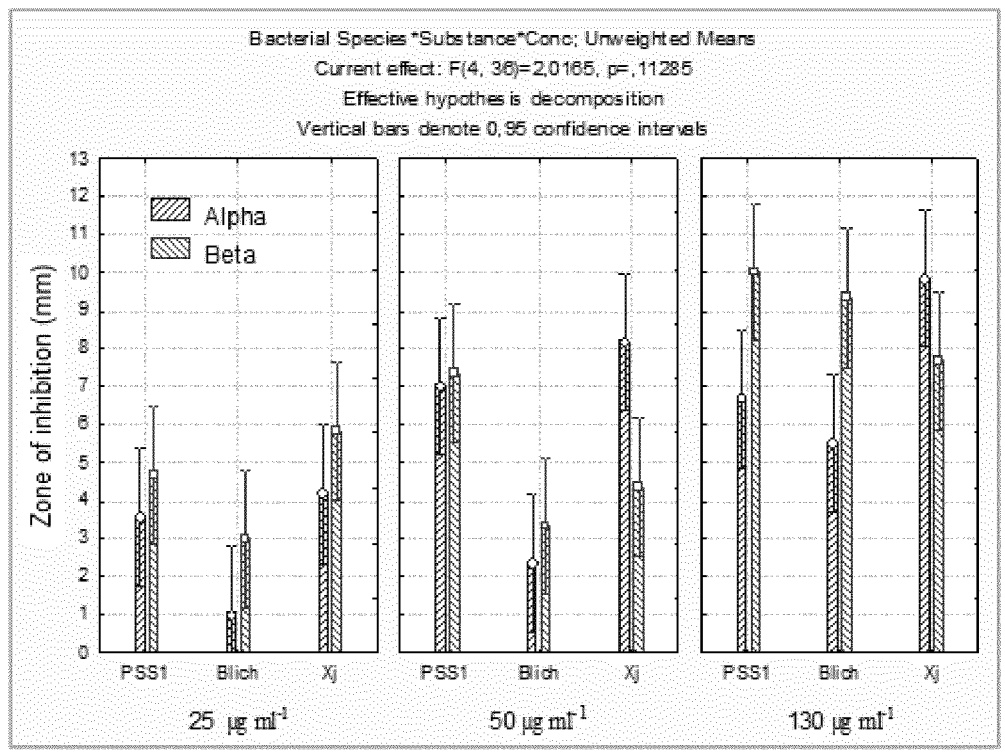
FIG. 3—Effect of polyamidoamine formulations α and β at different concentrations (25, 50 and 130 μg/ml) in inhibiting growth of *P. syringae* pv *syringae* (PSS1), *B. licheniformis* (Blich) and *Xanthomonas* spp. (Xj)—disaggregated data.

The disaggregated data in FIG. 3 show the effects of PAAs α and β and of their concentrations in terms of inhibition halo on the various bacterial species.

FIGS. 1, 2 and 3 relate to the same experiment, and show the main effects and interactions between the various factors tested: type of polyamidoamine (a or (3), polyamidoamine concentration (25, 50 or 130 µg/mL) and bacterial species (*P. syringae* pv *syringae* PSS1, *B. licheniformis* Blich and *Xanthomonas* spp. Xj).

Taken as a whole, the figures demonstrate that:

i) concentration has a significant and increasing effect on the inhibition halo for the bacterial species tested;

ii) PAA types α and β exhibit a different effect, according to the bacterial species: on average, β is more effective against species PSS1 and Blich, while α is more effective against Xj;

iii) the effect found is mainly due to the concentration.

Figure 4:
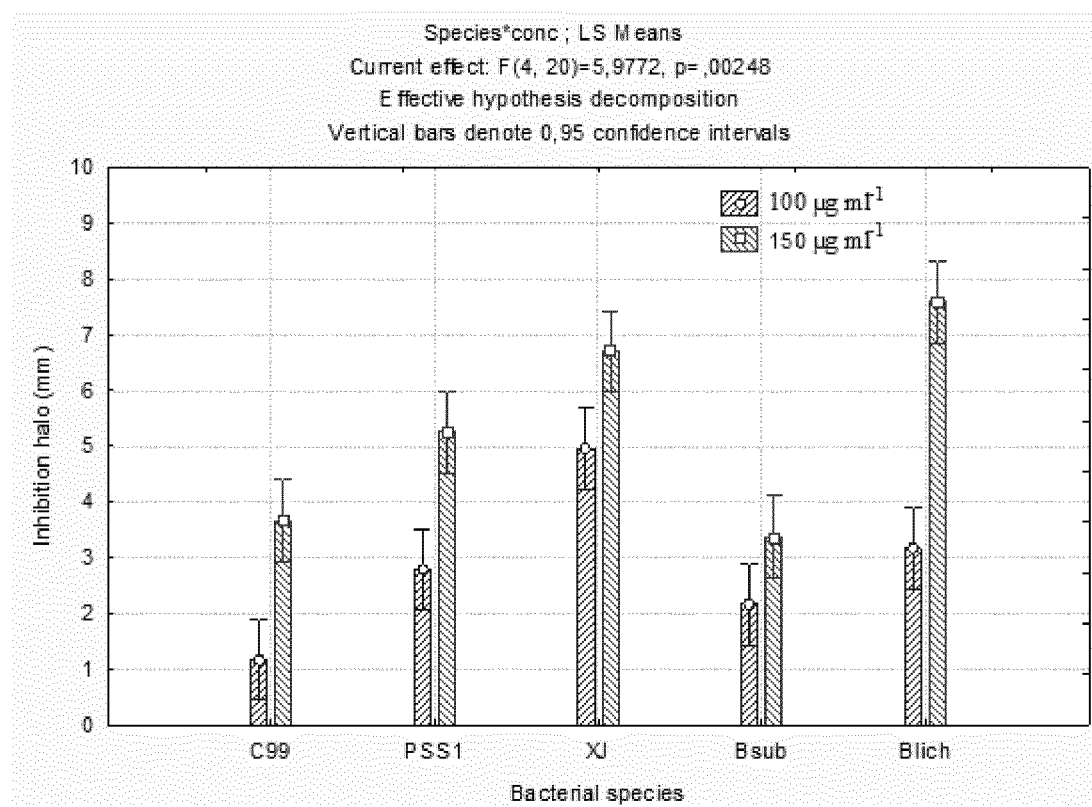
FIG. 4—Effect of polyamidoamine β concentration (100 and 150 μg/ml) on inhibition halo (in mm) of different bacterial species: C99=*Pseudomonas* spp; Bsub=*B. subtilis*; Blich=*B. licheniformis*; PSS1=*P. syringae* pv *syringae*; XJ=*Xanthomonas* spp.

FIG. 4 shows the effect of PAA β at concentrations of 100 and 150 µg/ml against the bacterial species C99=*Pseudomonas* spp; Bsub=*B. subtilis*; Blich=*B. licheniformis*; PSS1=*P. syringae* pv *syringae*; XJ=*Xanthomonas* spp.

Figure 5:
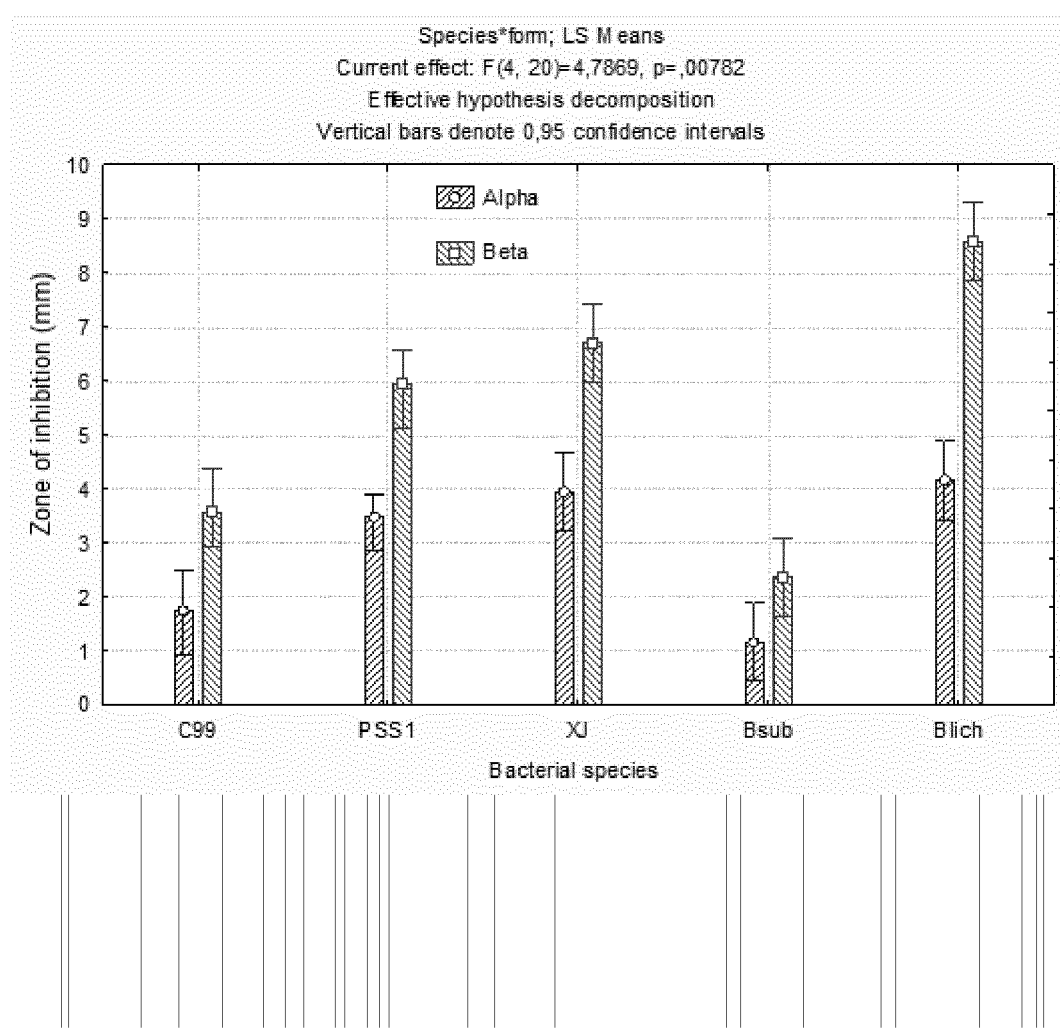
FIG. 5—Effect of polyamidoamine α and β formulations at 150 μg/ml on inhibition halo of different bacterial species: C99=*Pseudomonas* spp; Bsub=*B. subtilis*; Blich=*B. licheniformis*; PSS1=*P. syringae* pv *syringae*; XJ=*Xanthomonas* spp.

FIG. 5 shows the effect of compounds α and β at the concentration of 150 µg/ml against the same bacterial species.

Figure 6:
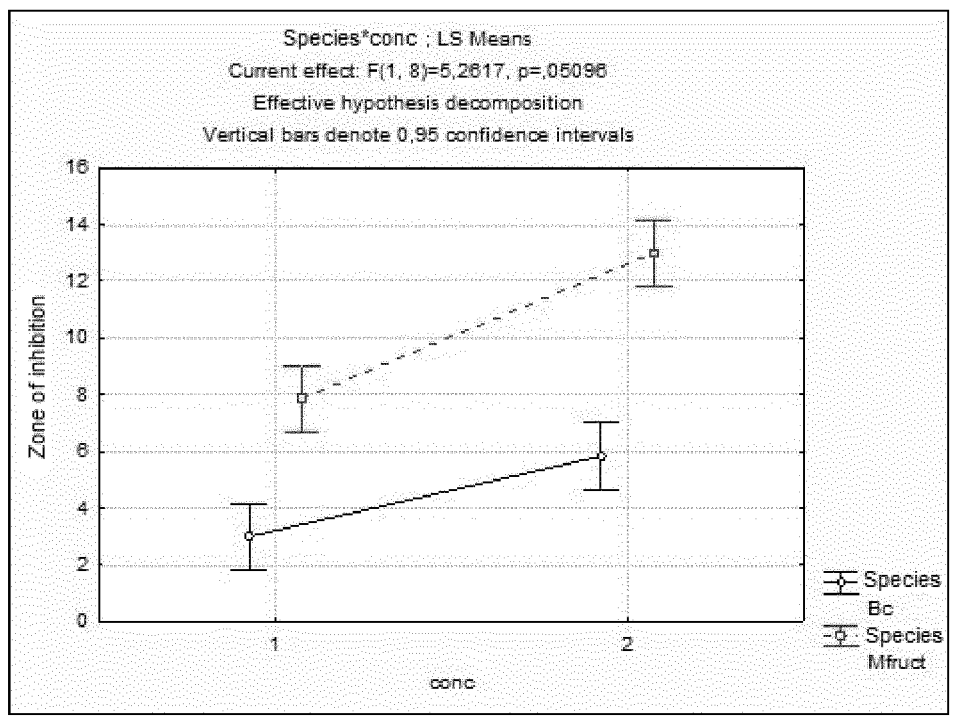
FIG. 6—Effect of different polyamidoamine concentrations (100 and 150 μg/ml) on inhibition halo (in mm) of the fungal species *Botrytis cinerea* (Bc) and *M. fructicola* (Mfruct). The data shown in the figure represent the mean of the data obtained with polyamidoamine formulations α and β.

At the concentrations of 100 and 150 µg/ml, the PAAs selected exhibit a strong growth-reducing power against *B. cinerea* and *M. fructicola*, which is significantly higher in the case of the latter (FIG. 6). The graph shows the mean of the results obtained with compounds α and β.

Figure 7:
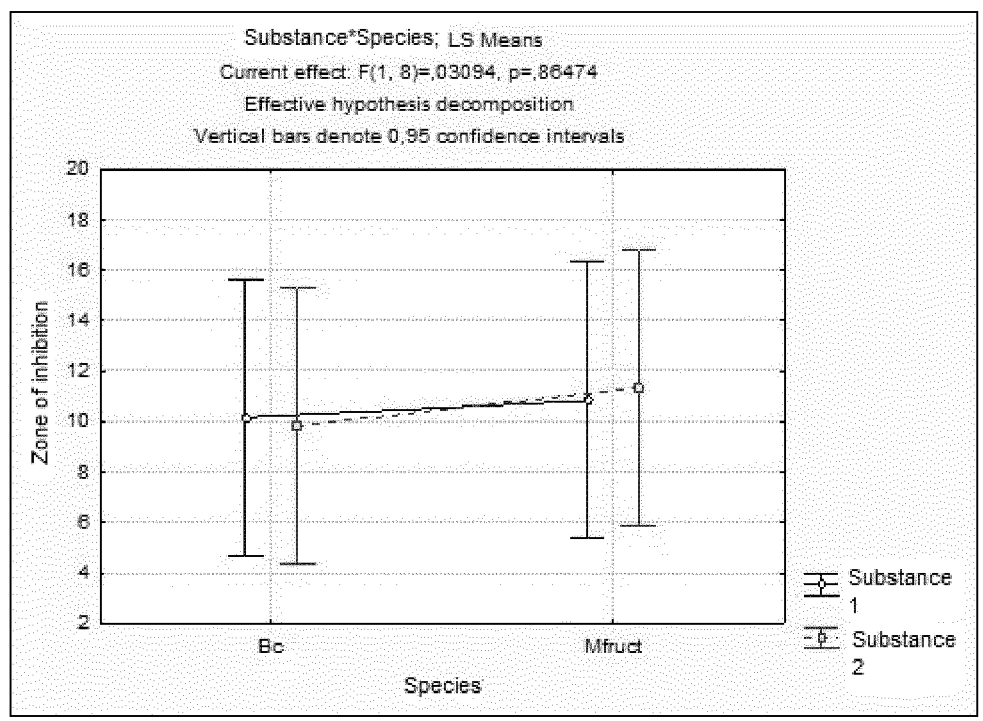
FIG. 7—Effect of polyamidoamine formulations (α=unbroken line; β=broken line) on inhibition halo of different fungal species (Bc=*Botrytis cinerea*; Mfruct=*Monilinia fructicola*). No significant differences were observed. The data shown in the figure represent the mean of the data obtained at different concentrations (100 and 150 μg/ml).

Unlike the findings for the bacterial species, no significant differences in effect between compounds α and β were observed for the fungal species tested (FIG. 7).

Figure 8:
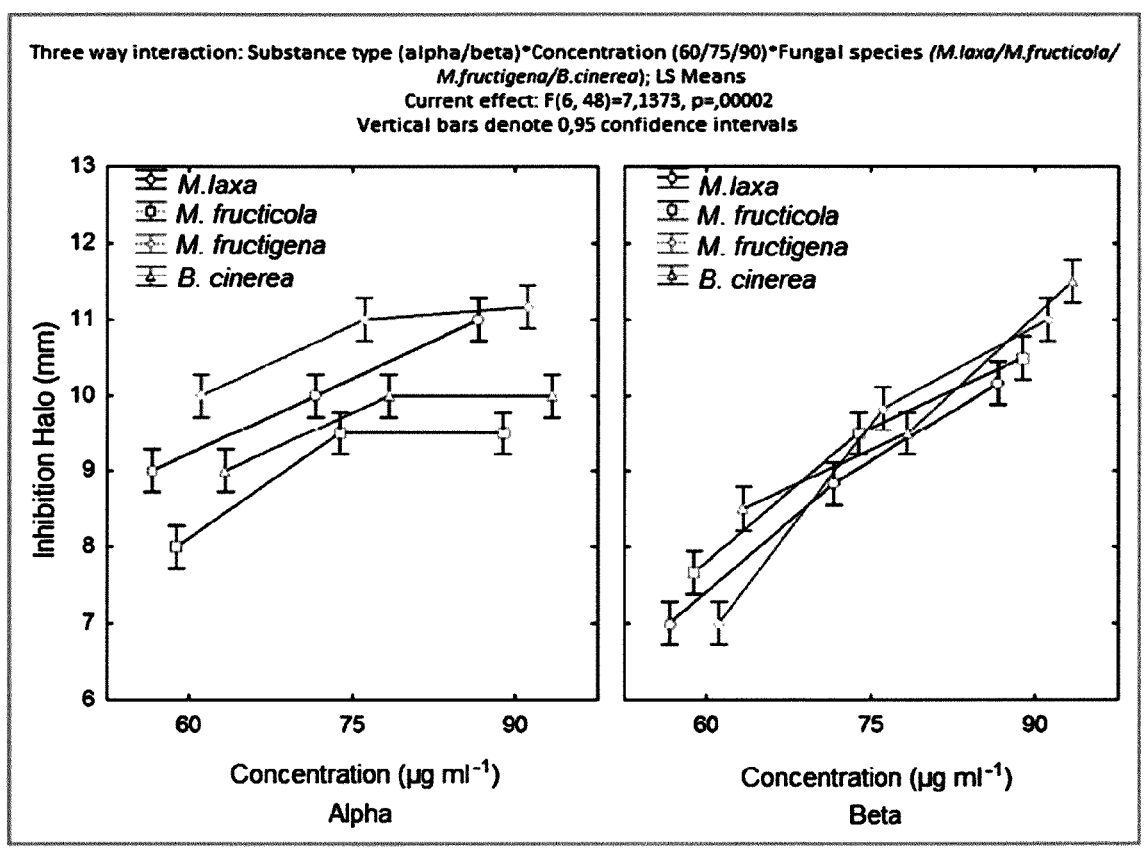
FIG. 8—Effect of polyamidoamine type (α, β) and concentration (60, 70 or 90 μg/ml) on inhibition halo of various post-harvest pathogenic fungi.

Tests conducted at lower concentrations and on a larger number of post-harvest pathogenic fungi (*M. laxa, M. fructicola, M. fructigena* and *B. cinerea*) (FIG. 8) indicate that at 60 µg/ml, PAA α gives rise to a larger inhibition halo than PAA β; PAA α does not exhibit a significant increase in the inhibition halo when the concentration is increased to 75 and 90 µg/ml, whereas PAA β exhibits an inhibitory trend proportional to the concentration, equaling and sometimes exceeding the values obtained with PAA α.

Figure 9:
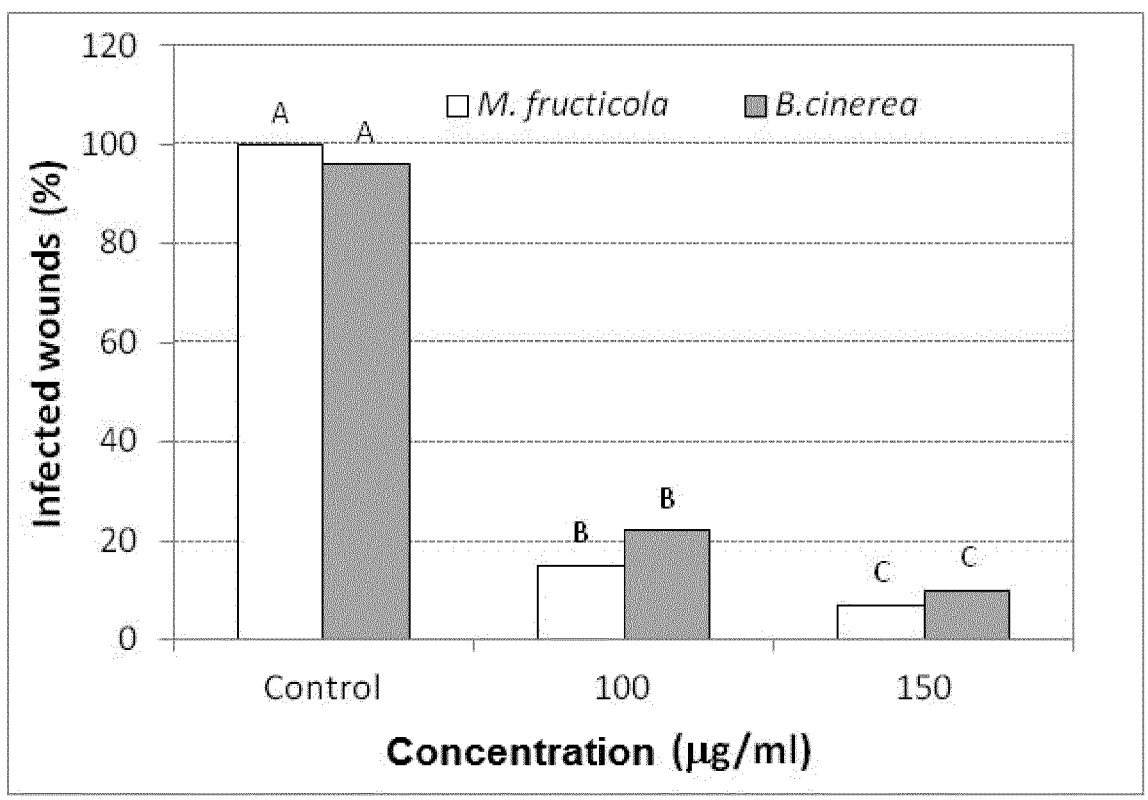
FIG. 9—Activity of polyamidoamine α at different concentrations in reducing the percentage of infected lesions on an apple inoculated with pathogens and treated with the substance (100 μg/ml) after two hours.

At the concentrations of 100 and 150 µg/ml, PAA α significantly reduced the percentage of infected lesions on apples inoculated with *M. fructicola* and *B. cinerea* (FIG. 9).

Figure 10:
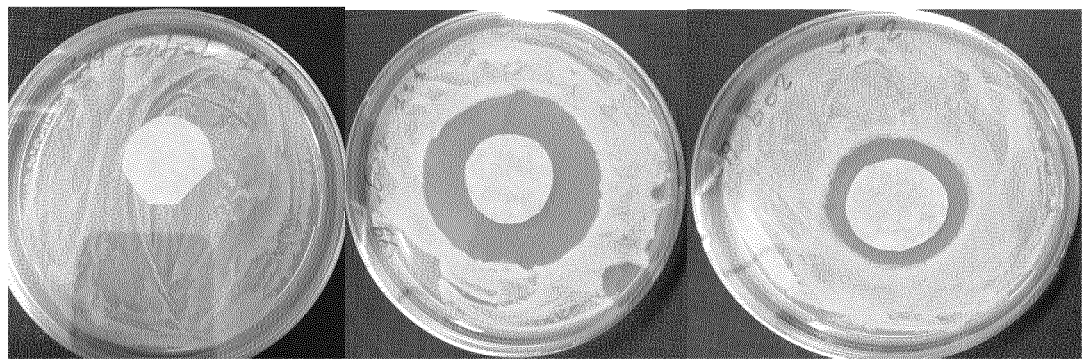
FIG. 10—Activity of polyamidoamine α in inhibiting growth of *Pseudomonas* spp., strain C99. A=untreated control; B=150 μg/ml; C=100 μg/ml.

Finally, FIG. 10 shows the activity of PAAs α in inhibiting the growth of *Pseudomonas* spp., strain C99.

On the whole, all the experiments indicate a clear, strong antibacterial and antifungal action by the PAAs examined.

The invention claimed is:

1. Polyamidoamines having a number average molecular weight ranging between 1,000 Da and 200,000 Da, obtained by copolyaddition of N,N-methylenebisacrylamide, glycine and agmatine and having the following formula (I):

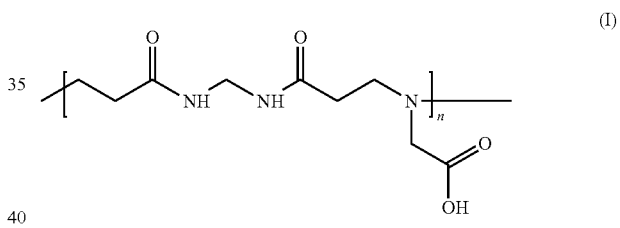

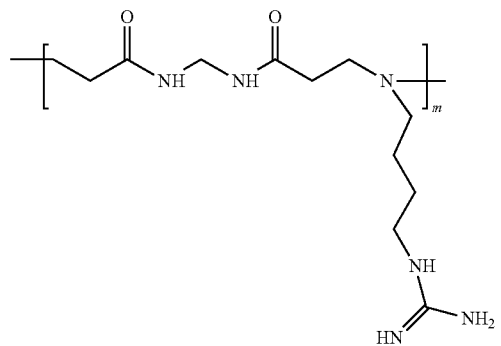

wherein n and m are two numbers such that the value (n+m) can range from 5 to 1,000, and wherein the ratio n/m is 0.6.

2. Polyamidoamines having a number average molecular weight ranging between 1,000 Da and 200,000 Da, obtained by copolyaddition of N,N-methylenebisacrylamide, glycine and agmatine and having the following formula (I):

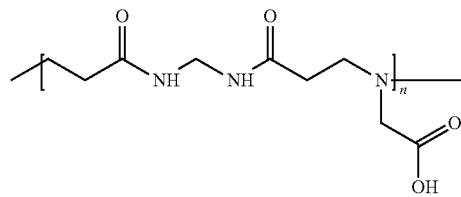
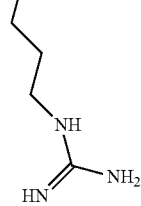

wherein n and m are two numbers such that the value (n+m) can range from 5 to 1,000, and wherein the ratio m/(n+m) ranges between 0.25 and 0.7.

3. Polyamidoamines according to claim 1, having a number average molecular weight ranging between 5,000 Da and 30,000 Da.

4. Polyamidoamines according to claim 1, for use in the treatment of infections caused by *E. coli, S. aureus, Xanthomonas* spp., *Pseudomonas syringae* pv. *Syringae, Bacillus licheniformis, B. subtilis, Pseudomonas* sp., *Monilia laxa, Monilia fructigena, Botrytis cinerea* and *Monilinia fructicola*.

5. Pharmaceutical compositions comprising a compound according to claim 1 in admixture with a pharmaceutically acceptable excipient and/or carrier.

6. A method of treatment of infections caused by *E. coli, S. aureus, Xanthomonas* spp., *Pseudomonas syringae* pv. *Syringae, Bacillus licheniformis, B. subtilis, Pseudomonas* sp., *Monilia laxa, Monilia fructigena, Botrytis cinerea* and *Monilinia fructicola* with a medicament comprising polyamidoamines according to claim 1.

* * * * *